United States Patent [19]

Bashkirov

[11] 4,146,837
[45] Mar. 27, 1979

[54] APPARATUS FOR DETECTING AND RECORDING SURFACE AND INTERNAL FLAWS

[75] Inventor: Valentin N. Bashkirov, Irkutsk, U.S.S.R.

[73] Assignee: Irkutsky Filial Vsesojuznogo Nauchnoissledovatelskogo I Proektnogo Instituta Aluuminievoi Magnieovi I Elektrodonoi Promyshlennosti, U.S.S.R.

[21] Appl. No.: 791,153

[22] Filed: Apr. 26, 1977

[51] Int. Cl.$^2$ .......................................... G01R 33/12
[52] U.S. Cl. .................................... 324/225; 324/227; 324/232; 324/238
[58] Field of Search .................. 324/37, 40, 225, 227, 324/232, 238

[56] References Cited

U.S. PATENT DOCUMENTS

| | | | |
|---|---|---|---|
| 1,946,196 | 2/1934 | Drake et al. | 324/37 |
| 2,729,785 | 1/1956 | Keevil | 324/37 |
| 3,290,167 | 12/1966 | Wood et al. | 324/37 |
| 3,340,466 | 9/1967 | Ono | 324/40 |

FOREIGN PATENT DOCUMENTS

| | | | |
|---|---|---|---|
| 171639 | 11/1965 | U.S.S.R. | 324/37 |
| 386330 | 9/1973 | U.S.S.R. | 324/37 |

Primary Examiner—Robert J. Corcoran
Attorney, Agent, or Firm—Steinberg & Blake

[57] ABSTRACT

The proposed structural flaw detector is intended for nondestructive testing of continuously moving electrically conducting products, e.g. aluminum, copper and other rods, and comprises two eddy current transducers spaced apart along the path of movement of the products being monitored. One of these transducers is a high-frequency one and is mounted first to detect flaws on the surface, while the other transducer is a low-frequency one and is mounted downstream of the first one to detect structural flaws occurring at a depth under the surface.

Arranged between the measuring channels of these transducers is a gating unit blocking the channel of the low-frequency transducer when a surface flaw is detected.

6 Claims, 4 Drawing Figures

APPARATUS FOR DETECTING AND RECORDING SURFACE AND INTERNAL FLAWS

The present invention relates to instruments for nondestructive testing, in which use is made of eddy currents to detect surface or subsurface structural flaws in elongate electrically conducting objects, and more particularly to eddy current testing instruments in which use is made of high-frequency and low-frequency eddy currents with automatic detection and separate recording of surface and subsurface structural flaws. The invention is aimed at obviating the various difficulties encountered in instruments of this type.

It has become standard practice to scan objects in order to detect surface and/or subsurface structural flaws by means of an excitation field of a certain frequency. However, the existing methods and means for eddy current scanning of elongate electrically conducting objects cannot be used for separate detection of surface and subsurface structural flaws.

In the prior art, it has been known to propose the use of high- and low-frequency eddy currents for detecting surface and subsurface flaws in a nondestructive manner.

A prior art device (cf. US Pat. No. 3,340,466; Cl. 324-40) comprises high- and low-frequency oscillators, an eddy current transducer, a gating means with a clock, high- and low-frequency measuring channels, and a recorder. In this device for separate detection of surface and subsurface structural flaws, the operation of the high- and low-frequency measuring channels is controlled in accordance with the operation of the clock which synchronizes the operation of the excitation oscillators. As a result, in the presence of surface flaws of particular dimensions, both measuring channels are activated producing information on the simultaneous occurrence of both a surface and a subsurface flaw. In this case, individual portions of the object under test are not checked simultaneously for surface and subsurface flaws. The accuracy of separate detection of surface and subsurface flaws by this known device seems to be insufficient.

It is an object of the present invention to obviate the above disadvantages and to provide a highly accurate testing instrument for separate detection of surface and subsurface structural flaws in elongate scanned workpieces.

The problem of modifying the system of processing signals coming from surface as well as subsurface structural flaws so as to provide for fast and separate detection of such flaws, constitutes the background of the present invention.

With these and other objects in view, there is proposed a structural flaw detector for nondestructive testing of the internal and external structure of continuously moving electrically conducting workpieces, with use being made of eddy currents, comprising a generator of high- and low-frequency signals selected so as to provide for interaction with the surface and subsurface flaws in a workpiece, eddy current transducers converting these signals to eddy currents interacting with the fields induced in the structural flaws, and measuring channels at the output of said eddy current transducers, transmitting the flaw signals to recording devices, said eddy current transducers being spaced apart along the path of movement of the workpieces so that the high-frequency transducer intended for detecting surface flaws is arranged first and the low-frequency transducer is arranged second, and a gating unit with a gate signal generator being connected between the measuring channels of the spaced transducers, which signal blocks the measuring channel of the low-frequency transducer as soon as a flaw signal appears from the high-frequency transducer.

Such an embodiment permits, first of all, enhancing the accuracy of separate detection of surface and subsurface flaws owing to the fact that the gating circuit producing a gate signal is controlled by the flaw signals arriving from the eddy current transducers as flaws occur in the workpiece.

In addition, depending on the flaws dimensions and depth of their occurrence, the gating circuit precludes false triggering of surface and subsurface flaw recorders, which is of particular importance under conditions of fast monitoring of elongate workpieces.

In accordance with other embodiments of the present invention, a structural flaw detector is proposed, characterized in that its gating unit includes threshold devices inserted between the measuring channels of the high- and low-frequency transducer and said gate signal generator, whose output is connected to a gating amplifier associated with the output of the low-frequency transducer measuring channel.

Such an embodiment of the gating unit permits optimizing the operation of the measuring channels of the high- and low-frequency transducers, which is so coordinated that signals carrying false information on the structure of the workpieces are eliminated.

According to a further feature of the invention, there is proposed a structural flaw detector characterized in that connected to the input of said gate signal generator is a source of a voltage proportional to the speed of the workpiece, comprising a speed sensor and a dc amplifier.

This embodiment is of particular advantage in cases where non-stop operation of the structural flaw detector is ensured when the flaw detected by the high-frequency transducer has not activated the low-frequency transducer. In this case, with the aid of the speed sensor and a dc amplifier, a signal is produced enabling the low-frequency transducer channel.

And, finally, according to yet another feature of this invention, there is proposed a structural flaw detector characterized in that each threshold device includes a Schmitt trigger connected to the input of a differentiator associated with the input of the gate signal generator.

This is one of the most effective ways of embodying the gating unit used in the proposed flaw detector.

The invention will now be described in greater detail with reference to preferred embodiments thereof, taken in conjunction with the accompanying drawings, wherein.

Separate detection of surface and subsurface structural flaws in elongate scanned electrically conducting workpieces is carried out with the aid of two separate eddy current transducers energized directly from a generator of continuous oscillations of high and low frequency and spaced apart along the length of a workpiece so that the high-frequency eddy current transducer is placed first, followed by the low-frequency transducer. The flaw signals at the outputs of high- and low-frequency measuring channels are used for automatic, depending on the scanning rate, control of a special gating circuit which produces a disabling gate pulse blocking the output of the low-frequency measuring channel for the period during which surface structural flaws pass through the working area of the low-frequency eddy current transducer.

Figure 1:
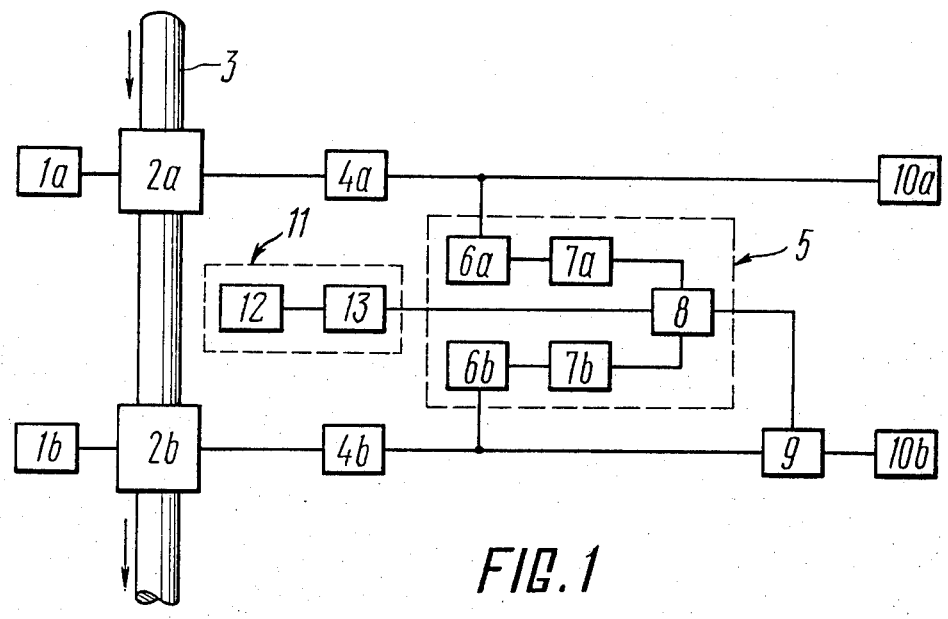
FIG. 1 is a schematic of a structural flaw detector according to the invention.

Referring now to FIG. 1, the flaw detector comprises a high-frequency oscillator 1a and a low-frequency oscillator 1b connected whereto, respectively, are excitation coils of noncontact eddy current transducers 2a and 2b of high and low frequency, respectively. The transducers are spaced a certain distance apart along the axis of a workpiece 3, in the direction of its movement. The transducers 2a and 2b also have sensing coils connected, respectively, to the inputs of high- and low-frequency measuring channels 4a and 4b, respectively, whose outputs are coupled to a gating unit 5 the input stages whereof, are, essentially, threshold devices 6a and 6b respectively provided with Schmitt triggers having their outputs connected to differentiators 7a and 7b associated with a generator 8 of a disabling gate pulse, the output of the latter being connected to an input of a gating amplifier 9 whose other input is coupled to the output of the low-frequency measuring channel 4b. The outputs of the high-frequency measuring channel 4a and gating amplifier 9 are connected, respectively, to surface and subsurface structural flaw recorders 10a and 10b. A speed-proportional voltage source 11 includes a scanning speed sensor 12 connected via a dc amplifier 13 to the disabling gate pulse generator 8.

Figures 2, 3, 4:
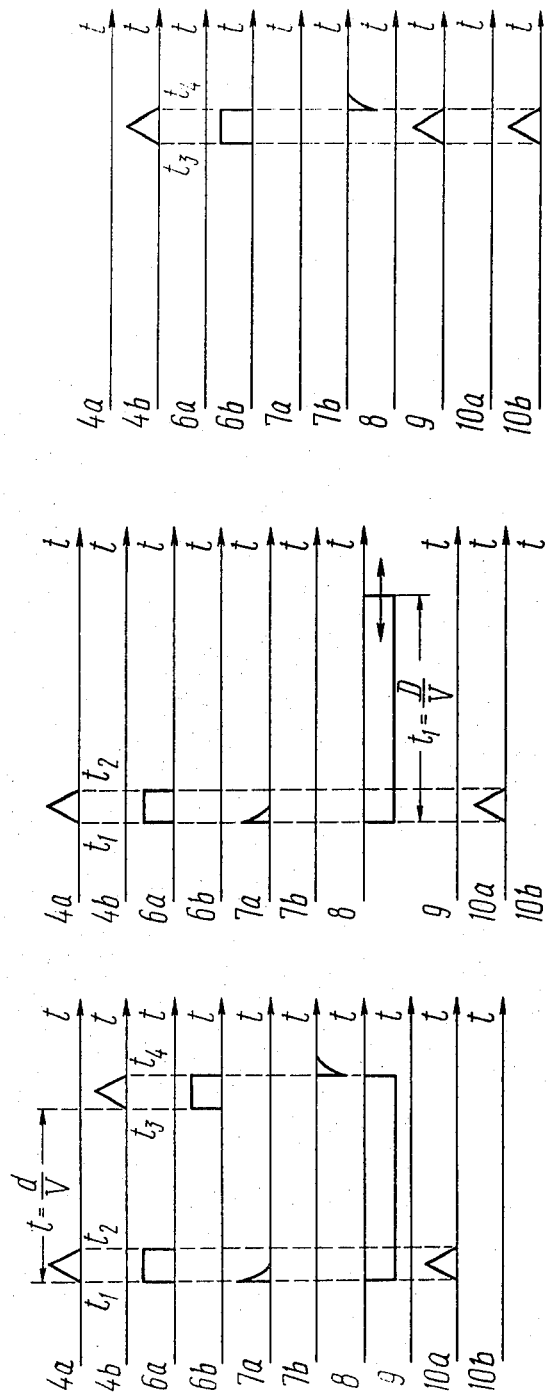
FIG. 2 shows graphically the operation of the structural flaw detector, with voltages being taken at various points of the detector of FIG. 1, in the case of occurrence of a large surface flaw.
FIG. 3 shows same as FIG. 2 in the case of occurrence of a surface flaw of the same dimensions with only the high-frequency eddy current transducer reacting thereto.
FIG. 4 shows same as FIG. 2 in the case of occurrence of a subsurface flaw.

The proposed flaw detector operates as follows:

From the oscillators 1a and 1b producing continuous oscillations whose carrier frequencies are selected according to the diameter and physical properties of the workpiece material, high- and low-frequency voltages are applied, respectively, to the excitation coils of the eddy current transducers 2a and 2b. Should a large surface flaw (FIG. 2) appear in the workpiece 3, the high-frequency eddy current transducer 2a arranged first in the direction of scanning of the workpiece 3 operates, and a signal appears at moment $t_1$ in the high-frequency measuring channel 4a, which is applied to the input of the recorder 10a and, at the same time, to the first input of the gating unit 5, namely, to the circuit of the trigger pulse for the disabling gate pulse generator 8. At moments $t_1$ and $t_2$, a square pulse is shaped at the output of the threshold device 6a and, via the differentiator 7a, a trigger pulse is shaped from the leading edge of the pulse at the threshold device 6a for the disabling gate pulse generator 8 which operates and blocks the gating amplifier 9 by the leading negative edge. After interval $t = d/V$ (where d is the distance between the front boundaries of the working areas of the transducers 2a and 2b, and V is the scanning speed), the low-frequency eddy current transducer 2b arranged downstream of the high-frequency transducer operates, and a signal appears at moment $t_3$ in the low-frequency measuring channel 4b, which is applied, at the same time, to the second input of the gating unit 5, namely, to the reset pulse circuit for the disabling gate pulse generator 8, and further to the signal input of the gating amplifier 9 which, by moment $t_3$, is blocked by the gate pulse from the generator 8 for the period of time it takes the surface flaw to pass through the working area of the low-frequency eddy current transducer 2b.

The signal from the low-frequency measuring channel 4b is applied via the gating amplifier 9 to the recorder 10b.

A square pulse is formed at the output of the threshold device 6b in the reset pulse circuit at moments $t_3$ and $t_4$, and at moment $t_4$ marking the end of transit of the surface flaw through the working area of the low-frequency eddy current transducer 2b, a reset pulse is formed through the differentiator 7b by the trailing edge of the pulse at the threshold device 6b, i.e., the gating amplifier 9 is enabled.

The maximum width of the gate pulse at any scanning speed is set somewhat greater than $T = D/V$ by means of the voltage applied from the scanning speed sensor 12 via the dc amplifier 13 to the gate pulse generator 8 (D being the distance including the front and rear boundaries of the working areas of both eddy current transducers 2a and 2b).

In the case where a surface flaw passes whose dimensions are such that only the high-frequency transducer 2a (FIG. 3) reacts thereto, a signal appears at moment $t_1$ in the high-frequency measuring channel 4a, which is applied to the input of the recorder 10a and, at the same time, to the threshold device 6a at whose output a square signal is formed at moments $t_1$ and $t_2$, its leading edge triggering, at moment $t_1$ via the differentiator 7a, the gate pulse generator 8, and the gating amplifier 9 is blocked for a period of time it requires the surface flaw to transit the working area of the low-frequency eddy current transducer 2b.

In the absence of a reset pulse, the gate pulse generator 8 is reset automatically since the maximum width of the gate pulse at any scanning speed is set slightly greater than $T = D/V$ by the voltage applied from the scanning speed sensor 12 via the $d_c$ amplifier 13 to the gate pulse generator 8.

In the case of a subsurface structural flaw (FIG. 4), only the low-frequency transducer 2b operates and at the output of the low-frequency measuring channel 4b there appears a signal which is applied, via the unblocked gating amplifier 9, to the recorder 10b, and the shaped reset pulse does not act upon the gate pulse generator 8 through the threshold device 6b and differentiator 7b.

It will thus be seen that the structure of the invention includes a high-frequency detecting means 2a for detecting surface flaws and a low-frequency detecting means 2b for detecting internal flaws, the pair of detecting means 2a and 2b being arranged in such a way that the article 3 which is to be scanned is first scanned by the high-frequency detecting means and then by the low-frequency detecting means. A high-frequency circuit means which includes the high-frequency measuring channel 4a interconnects the high-frequency detecting means 2a with a surface-flaw recording means 10a, while a low-frequency circuit means, which includes the low-frequency measuring channel 4b and the gating amplifier 9 interconnects the low-frequency detecting means 2b with an internal flaw recording means 10b. The gating unit 5 forms a blocking-and-resetting circuit means electrically connected between the high-frequency circuit means and low-frequency circuit means for blocking operation of the low-frequency circuit means, to prevent operation of the internal flaw recording means 10b, when the high-frequency detecting means detects a surface flaw and for resetting the low-frequency circuit means to resume operation of the internal flaw recording means 10b when the surface flaw detected by the high-frequency detecting means 2a is subsequently detected by the low-frequency detecting means 2b. The speed-responsive voltage source 11 forms a speed-responsive timing means operatively connected to the blocking-and-resetting circuit means 5 for actuating the latter to reset the low-frequency circuit means in the event that the high-frequency detecting means 2a detects a surface flaw which is too small to be detected by the low-frequency detecting means 2b, this speed-responsive timing means 11 bringing about a resetting of the low-frequency circuit means through the blocking-and-resetting circuit means 5 after an interval sufficient for the surface flaw which was too small to be detected by the low-frequency detecting means 2b to become situated beyond the latter.

I claim:

1. In an apparatus for detecting and recording both surface and internal flaws in an elongated electrically-conductive article, high-frequency detecting means for detecting surface flaws and low-frequency detecting means for detecting internal flaws, said high-frequency and low-frequency detecting means being arranged with respect to each other and an article scanned thereby in such a way that the article is longitudinally scanned first by said high-frequency detecting means and then by said low-frequency detecting means, surface-flaw recording means for recording the presence of surface flaws in the article, internal flaw recording means for recording internal flaws in the article, high-frequency circuit means electrically interconnecting said high-frequency detecting means with said surface flaw recording means for operating the latter to record surface flaws detected by said high-frequency detecting means, low-frequency circuit means electrically interconnecting said low-frequency detecting means with said internal flaw recording means for operating the latter to record internal flaws detected by said low-frequency detecting means, and blocking-and-resetting circuit means electrically connected between said high-frequency circuit means and low-frequency circuit means for blocking operation of said internal flaw recording means by said low-frequency circuit means when said high-frequency detecting means detects a surface flaw and for resetting said low-frequency circuit means to resume operation of said internal flaw recording means when a surface flaw previously detected by said high-frequency detecting means is subsequently detected by said low-frequency circuit means.

2. The combination of claim 1 and wherein a speed-responsive timing means which responds to the speed with which an article is scanned is electrically connected with said blocking-and-resetting circuit means for actuating the latter to reset said low-frequency circuit means to resume operation of said internal flaw recording means after an interval great enough for a surface flaw detected by said high-frequency detecting means to have been scanned by said low-frequency detecting means, so that in the event that a surface flaw detected by said high-frequency circuit means is too small to provide a response at said low-frequency detecting means, said low-frequency circuit means will nevertheless be reset to resume operation of said internal flaw recording means by said low frequency detecting means.

3. The combination of claim 1 and wherein said high-and-low-frequency detecting means are respectively in the form of a high-frequency eddy current transducer and a low-frequency eddy current transducer.

4. The combination of claim 3 and wherein said high-frequency circuit means includes a high-frequency measuring channel electrically connected between said high-frequency detecting means and said surface flaw recording means while said low-frequency circuit means includes a low-frequency measuring channel and a gating amplifier connected in series between said low-frequency detecting means and said internal flaw recording means with said gating amplifier being situated between said low-frequency measuring channel and said internal flaw recording means, said blocking-and-resetting circuit means including a pair of threshold devices one of which is electrically connected to said high-frequency circuit means between said high-frequency measuring channel and said surface flaw recording means and the other of which is connected to said low-frequency circuit means between said low-frequency measuring channel and said gating amplifier, said blocking-and-resetting circuit means further including a pair of differentiators respectively electrically connected to said pair of threshold devices to receive outputs therefrom, and a disabling gate pulse generator electrically connected between said differentiators to receive outputs therefrom, said disabling gate pulse generator being electrically connected to said gating amplifier to transmit the output of said disabling gate pulse generator to said gating amplifier, the latter having a pair of inputs one of which receives the output from said disabling gate pulse generator and the other of which receives the output from said low-frequency measuring channel, said gating amplifier having its output connected to said internal flaw recording means.

5. The combination of claim 4 and wherein said disabling gate pulse generator has a third input in addition to two inputs thereof which respectively receive the outputs of said differentiators, and voltage source means responsive to the speed with which an article is scanned by said high-and-low frequency detecting means and electrically connected to said third input of said disabling pulse generator for acting on the latter to terminate blocking of said gating amplifier after an interval sufficient for a surface flaw detected by said high-frequency detecting means to be scanned by said low-frequency detecting means, so that in the event that such a surface flaw is too small to provide a response at said low-frequency detecting means said low-frequency circuit means will nevertheless be reset to resume operation of said internal flaw recording means by said low-frequency detecting means by the time that such a small surface flaw has been scanned by said low-frequency detecting means.

6. The combination of claim 5 and wherein said voltage source means includes a scanning speed sensor and a dc amplifier connected in series between said scanning speed sensor and said disabling gate pulse generator.

* * * * *